United States Patent [19]

Henrie

[11] 4,170,455

[45] Oct. 9, 1979

[54] GAS MONITORING METHOD AND APPARATUS THEREFOR

[75] Inventor: James O. Henrie, Hidden Hills, Calif.

[73] Assignee: Rockwell International Corporation, El Segundo, Calif.

[21] Appl. No.: 665,738

[22] Filed: Mar. 11, 1976

[51] Int. Cl.$^2$ .................... G01N 25/20; G01N 31/10
[52] U.S. Cl. ................ 23/232 R; 23/232 E; 73/25; 422/83; 422/94; 422/95; 422/98
[58] Field of Search .......... 23/232 R, 254 R, 232 E, 23/254 E, 255 R, 255 E; 73/23, 25, 26, 27 R; 422/83, 94, 95, 98

[56] References Cited

U.S. PATENT DOCUMENTS

| | | | |
|---|---|---|---|
| 2,296,030 | 9/1942 | Hall | 73/25 |
| 2,888,330 | 5/1959 | Kapff | 23/254 E X |
| 2,916,358 | 12/1959 | Valentine et al. | 23/254 E |
| 3,057,693 | 10/1962 | Barnes et al. | 23/232 E |
| 3,567,394 | 3/1971 | Betz | 23/232 E |

Primary Examiner—Joseph Scovronek
Attorney, Agent, or Firm—L. Lee Humphries; Henry Kolin; Clark E. DeLarvin

[57] ABSTRACT

A method and apparatus for monitoring the concentration of a component of a gas stream. The gas stream to be monitored is heated to a desired temperature and passed through an insulated gas passageway of a conduit member. The heated gas passes sequentially through a perforate metal shield and a body of a particulate catalyst. The temperature of the heated gas entering and leaving the conduit member is monitored and any increase in temperature is correlatable with the component concentration in the gas stream. The method and apparatus are particularly suitable for monitoring the concentration of hydrogen or oxygen in a gas stream.

12 Claims, 3 Drawing Figures

GAS MONITORING METHOD AND APPARATUS THEREFOR

BACKGROUND OF THE INVENTION

1. Field of the Invention

This invention relates to a gas monitoring method and apparatus, and more particularly to a method and apparatus for the determination and continuous monitoring of the degree or percentage purity of a gas stream. In a particularly preferred embodiment, the invention relates to a method and apparatus for monitoring the hydrogen or oxygen content of a gas stream.

2. Prior Art

In the detection or measurement of constituents of a gaseous mixture it has been known heretofore to compare the thermal conductivity of one gas stream with that of a gas of a known composition or so-called "standard" or "reference" gas. In making such a comparison, it is customary to employ two electrically heated thermally sensitive elements, such as temperature responsive resistors connected to the arms of a Wheatstone bridge. One of the resistance elements is in contact with the gas under observation, and the other is positioned in a sealed container of the standard or reference gas. Such a method has not been altogether satisfactory. The equilibrium temperature attained by the thermally sensitive elements depends principally upon the heat loss rate of each element and the ability of gas surrounding each element to conduct heat; the temperature being lower when the gas has a high thermal conductivity and higher when the gas has a low conductivity. If the temperature sensitive element has a high temperature coefficient of electrical resistance, this resistance will have a value dependent upon the gas thermal conductivity.

Thus, if two substantially identical temperature sensitive resistance elements are exposed to gases having different thermal conductivities, the quantities of heat given off or the rate of heat loss of each of these elements to the respective gases will be different. This difference will result in one of the resistance elements being maintained at a higher temperature than the other. The difference in temperature will in turn result in a difference in the resistance of the two elements, thereby causing deflection of a galvanometer in the bridge circuit and necessitate an adjustment of the bridge to produce a state of balance. The magnitude of adjustment will, of course, be dependent upon the differences between the thermal conductivities of the two gases.

An example of a gas analysis apparatus in which the need for a reference gas has been eliminated is shown in U.S. Pat. No. 2,296,030. In accordance with the apparatus disclosed therein, both of the temperature sensitive devices are immersed in spaced relation in the gas under investigation. A perforated shield or baffle member is mounted between the two temperature sensitive devices to reduce radiation. Heat is applied to one of the temperature sensitive devices and under such condition that the temperature variation between the two devices is a function of the thermal conductivity of the gas. The ratio of the temperatures is measured by any suitable means such as a mercury thermometer or temperature sensitive resistance elements connected in a bridge circuit.

Thermal conductivity devices have not been altogether satisfactory. The reliability and accuracy of such devices are affected by numerous variables such as changes in flowrates of the gas stream, pressure, concentration of water vapor present, as well as other changes in the gas composition, all of which affect the thermal conductivity of the gas. Thus, the accuracy of such devices generally is poor, and the electrical circuitry required to attempt to compensate for all the variables is quite complicated.

In U.S. Pat. No. 3,567,394 there is depicted a system for determining impurity concentrations in a gaseous atmosphere. A known impure gaseous stream and an unknown impure gaseous stream are passed through parallel conversion zones to produce separate conversion product streams. The separate conversion product streams then are passed through detection devices, and the signal generated from such devices is quantitatively correlated with the impurity content of the unknown stream. The disadvantage of the disclosed system is that it requires a gaseous stream with a known impurity and in addition involves complex multiple flow paths.

U.S. Pat. No. 3,057,693 discloses yet another method and apparatus for monitoring mixed gas streams. In the apparatus disclosed therein, a container in which thermister bolometer flakes are mounted, is provided with inlet-outlet ports for receiving a small flow of a gas stream which is to be monitored. One or both of the flakes are covered with thin diaphragms which may be in the form of tiny cups with suitable electrical insulation. On one of the two diaphragms, or a single one if only one is used, there is placed a small amount of finely divided solid which reacts with the constituent in the gas stream which is to be monitored or which is a catalyst for the reaction of the constituent either with itself or with other constituents of the gas stream.

The reaction of the constituent of the gas to be detected produces heat or removes it and so changes the temperature of the thermistor flake with which it is in heat-conducting contact, whereas the other flake adjusts itself to the average temperature of the gas stream. If there is any of the constituent to be monitored present in the gas stream, one of the flakes becomes hotter than the other and a signal results which, with conventional electronic processing, can be used for an indicating, recording, alarm or control means. A disadvantage of such a system is that it requires flow regulation and appears to be an inherently slow response, high drift device.

In U.S. Pat. No. 2,916,358 there is disclosed an apparatus for detecting carbon monoxide. The apparatus comprises a conduit through which the atmosphere to be tested is passed. Also, located within the conduit member is a thermistor juxtaposed with an oxidizer and another thermistor juxtaposed with an inert material. The inert material and the oxidizer are sequentially contacted with the atmosphere to be tested. The thermistors are connected in an electrical circuit adapted to produce a signal indicative of the difference in temperature between the thermistors, and hence the quantity of carbon monoxide in the atmosphere. An essential part of the disclosed apparatus is a coil circumscribing the conduit member and in heat exchange relationship therewith, whereby the atmosphere to be tested passes through the coil and absorbs heat from the oxidizer zone prior to its entry into the conduit member. With such an arrangement the temperature of both thermistors will increase with increasing reactant concentrations. This, in turn, results in a slow response such that the apparatus would not appear capable of accurate quantitative measurement of fluctuating reactant concentrations.

In many chemical reactions or physical separations there is a production of continuous streams of mixed gaseous components, and it frequently is desirable or even necessary to determine the amount of one component which may be present in the gas stream in relatively small amounts. There still is need for an apparatus for such applications. Further, such apparatus should be capable of providing an accurate continuous response. There is a particular need for method and apparatus to continuously and reliably monitor the presence of oxygen or hydrogen, whichever is the lesser stoichiometric constituent and where both are present, in a gas stream. An application for such an apparatus exists, for example, in the field of water-cooled nuclear reactors where metal-water reactions and decomposition of the cooling water can occur to form free hydrogen and oxygen. The hydrogen and oxygen must be recombined, either for collection and return to the reactor containment or for disposal, to prevent the hydrogen concentrations reaching a combustible limit, which is about 4% hydrogen in air. Therefore, it is essential to have a reliable hydrogen/oxygen analyzer available to accurately indicate the amount of hydrogen present in the containment atmosphere.

SUMMARY OF THE INVENTION

In accordance with the present invention, there is provided a method and apparatus for continuously and reliably monitoring a component part of a gas stream. For convenience, the invention will be described with respect to monitoring the presence of oxygen or hydrogen in a gas stream. It will be apparent to those versed in the art, however, that the method and apparatus would have equal application with respect to other gas streams, such as, for example, monitoring the carbon monoxide constituent of a gas stream.

Broadly, the apparatus of the present invention comprises a conduit member, which is provided with a gas inlet means adjacent one end and a gas outlet means adjacent the other end. A gas inlet temperature sensor is located adjacent the gas inlet means for sensing the temperature of a gas stream entering the conduit member. A gas outlet temperature sensor is located adjacent the gas outlet means of the conduit member for sensing the temperature of the gas stream passing therethrough. Located in the conduit member intermediate the two temperature sensors is a body of a particulate catalyst material, which preferably is either platinum, palladium, or combinations thereof. Also located in the conduit member intermediate the gas inlet temperature sensor and the body of particulate catalyst material is at least one perforate heat shield for reducing the transfer of radiant thermal energy from the body of particulate catalyst material to the gas inlet temperature sensor. The apparatus further includes means for heating the gas stream to be monitored to a desired temperature prior to its entry into contact with the gas inlet temperature sensor. Preferably, the conduit member is formed from or surrounded by a thermal insulating material, and optionally, is further surrounded by a metal housing to provide structural support to and protection for the insulating material.

In operation, in accordance with the present method, the gas stream to be monitored first is cooled to remove excess water vapor, then heated to the desired temperature, which preferably is substantially above ambient temperature, to dry the gas or reduce its relative humidity. The heated gas stream then is introduced into a thermally insulated gas passageway of the conduit member where it first contacts the gas inlet temperature sensor for measuring or sensing the temperature of the gas stream. The gas stream then passes through the perforate metal heat shield and into contact with a bed of a particulate catalyst, the catalyst being selected, of course, to effect the desired reaction, depending upon the specific component of the gas stream to be monitored. The catalyst effects a reaction which in turn causes a change in gas temperature. The gas stream leaving the bed of particulate catalyst passes into contact with a second temperature sensor and then is discharged from the thermally insulated gas passageway.

The temperature difference between the inlet gas stream and the gas stream exiting the gas passageway is directly correlatable with the concentration of the component part of the gas stream. More particularly, since the heat capacity of various diatomic gases on a volume basis are all essentially the same, from about 0.179 to 0.181 BTU per cubic foot °F. at 68° F., the temperature rise for any mixture of such gases is directly proportional to the amount of heat added. The amount of heat added is directly proportional to the amount of, for example, hydrogen and oxygen available for combination. In addition, the overall accuracy of the method and apparatus may be improved by calibrating under actual operating conditions and correcting for the actual gas temperatures monitored for any given component concentration. It is an advantage of the present invention that the observed deviation from the theoretical value is small, thus a high degree of accuracy is readily obtainable.

Hydrogen and oxygen react in accordance with the general formula:

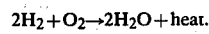

$$2H_2 + O_2 \rightarrow 2H_2O + \text{heat}.$$

Obviously, if the hydrogen and oxygen are present in the exact stoichiometric proportions represented above the temperature rise will be correlatable to the concentration of both the hydrogen and oxygen. Generally, however, there is a substantial excess of one and what is desired is to monitor the concentration of the other. In such instances the lesser constituent is completely reacted, and the amount of heat generated causes a rise in temperature which is indicative of its concentration.

The method and apparatus of the present invention possess certain features which are of vital importance to reliable and accurate operation. One feature is that by virtue of preheating the gas prior to its entry into contact with the first temperature sensor, any fluctuations in ambient temperature have substantially no effect on the overall sensitivity and accuracy of the measurements. Thus, it is not necessary to provide any elaborate controls over the ambient conditions or to attempt to compensate for temperature fluctuations by measuring those fluctuations and then, in some manner, attempting to correlate these fluctuations with the temperature difference observed in the gas passing through the apparatus. This in turn means that the method and apparatus may be practiced in the unfavorable environment of an operating plant, such as, for example, a nuclear reactor facility.

Another important feature is that the gas passes through a perforate heat shield, which is located intermediate the first temperature sensor and the bed of particulate catalyst. The heat shield serves to prevent, or substantially reduce, the transfer of radiant thermal energy from the catalyst to the first upstream temperature sensor, which would result in unreliable or inaccurate indications of the concentration of the component being monitored. The radiant heat energy absorbed by the heat shield is transferred by conduction and convection to the gas stream and appropriately adds to the temperature rise of the gas.

The method and apparatus can be used at relatively high and low flowrates. Except for heat losses, the temperature rise resulting from a particular gas passing through a catalyst bed, which reacts all of the minimum stoichiometric constituent, is independent of the gas flowrate. This is because the gas carrying the reactants is its own coolant. Therefore, if the catalyst bed is sized for the maximum flow which can occur, and if the calibration compensates for heat losses, the device is quite accurate over a wide range of flowrates. (The response time is shorter, of course, with higher flowrates.) Thus, the present invention is applicable to a wide range of flowrates and eliminates the necessity for a precision flow regulator. This in turn permits operation with a positive displacement blower or an inexpensive standard flow regulator in the conditions normally encountered in an operating plant.

DETAILED DESCRIPTION OF THE INVENTION

The present invention will be more clear with reference to the following discussion of the drawings which are set forth for the purpose of illustration only and should not be construed as limiting the scope of the invention.

Figure 1:
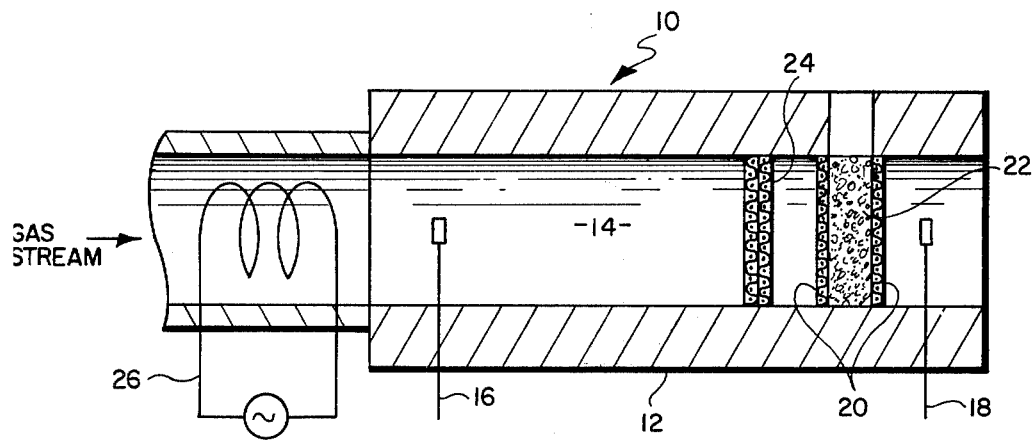
FIG. 1 is a schematic illustration of an apparatus of the present invention.

FIG. 1 is a schematic illustration of the present invention wherein the apparatus is designated by reference numeral 10. The apparatus comprises an elongated housing 12 having opposite ends and an axial gas passageway 14 therethrough. The apparatus is provided with an inlet temperature sensor 16 and an outlet temperature sensor 18. Downstream of inlet temperature sensor 16 there is provided in the gas passageway a perforate heat shield 24, which may be in the form of one or more perforate metal plates or screens, which permits the passage of gas therethrough, but substantially prevents the transfer of radiant thermal energy upstream to the inlet temperature sensor. The shield may be formed from any material which will resist attack by the constituents of the gas stream and is structurally stable at the inlet gas temperatures. Examples of preferred materials include ceramics, metals, asbestos, carbon and the like. The metals such as stainless steels are particularly preferred, since they are relatively inexpensive and readily formed into the desired shapes. Also, the shiny surface of stainless steels aids in reflecting the radiant energy downstream away from the inlet temperature sensor.

Intermediate perforate thermal heat shield 24 and outlet temperature sensor 18 is a body of particulate catalyst 22, which is retained in position by perforate catalyst support members 20. Generally, perforate support members 20 will comprise a metal mesh or screen having openings less than the size of the discrete catalyst particles. Preferably, the particulate catalyst will have a uniform size and a configuration to provide a bed of catalyst particles which has about a 40% void volume for the gas to pass through. Advantageously, the particulate catalyst bed will be cylindrical in shape and have a thickness-to-diameter ratio of from about 0.8:1 to 1.2:1 to maximize the bed volume-to-surface area ratio, thereby maximizing the flow capacity-to-heat loss ratio. The preferred catalyst materials are platinum, palladium and mixtures thereof. A particularly preferred catalyst for the hydrogen-oxygen reaction is a mixture of platinum and palladium which may be solid, but usually is in the form of a thin coating on an inert, porous substrate such as alumina.

Upstream of inlet temperature sensor 16, there is provided heating means 26 for heating the stream of gas to be monitored to a temperature above ambient, preferably substantially above ambient to provide a substantially dry gas, otherwise the moisture content of the gas may have a detrimental effect on the accuracy and reliability of the apparatus. By substantially dry gas, it is meant that the gas should be heated to a sufficiently high temperature to provide an effluent gas stream having a relative humidity of less than 10%. Particularly good results are obtained when the gas stream has a relative humidity of from about 1 to 5%. Another benefit obtained by heating the gas is that the effect of normal variations in the ambient temperature are minimized. Heating means 26 is depicted in FIG. 1 as an electrical resistance heater connected to a source of electrical power. However, it will be apparent to those versed in the art that numerous other means of heating could be provided, which may be direct or indirect heating, it only being essential that the heating means be capable of maintaining a substantially uniform inlet temperature under steady state conditions.

In operation the gas stream to be monitored is introduced into the apparatus 10, passing axially through passageway 14. It first passes through heating means 26, where the temperature of the gas stream is raised preferably substantially above ambient, such that any minor variation in the ambient temperature will have substantially little effect on the overall sensitivity and accuracy of the apparatus. Heating means 26, which may be any of numerous types known to those versed in the art, should be capable of maintaining a desired temperature at some substantially fixed point. That is to say, the temperature of the gas leaving heating means 26 should be maintained at a substantially uniform temperature. Heating means 26 should be capable of maintaining a desired temperature without any variation greater than about 1° F./min. and preferably less than about 0.1° F./min.

After being heated, the gas stream contacts inlet temperature sensor 16 and then passes through perforate metal shield 24, and through screens 20, which contain the bed of particulate catalyst 22.

In the bed of particulate catalyst, the hydrogen and oxygen in the gas stream react exothermically causing an increase in the temperature of the gas stream, which increase in temperature is monitored by outlet temperature sensor 18. The increase in temperature resulting from the exothermic reaction taking place within the bed of particulate catalyst is prevented from radiating upstream to inlet temperature sensor 16 by the perforate metal shields, the sensible heat being, of course, carried off by the gas stream. The incoming gas contains the reactants which generate heat and also acts as the coolant to carry away such heat. Therefore, except for thermal losses to ambient surroundings, the temperature rise monitored by the sensors is independent of flowrate. Thus, the present invention provides an apparatus and method having a high sensitivity and accuracy, and which does not require elaborate controls over the ambient condition or precise measurements of the flowrate of the gas entering the apparatus.

Figure 2:
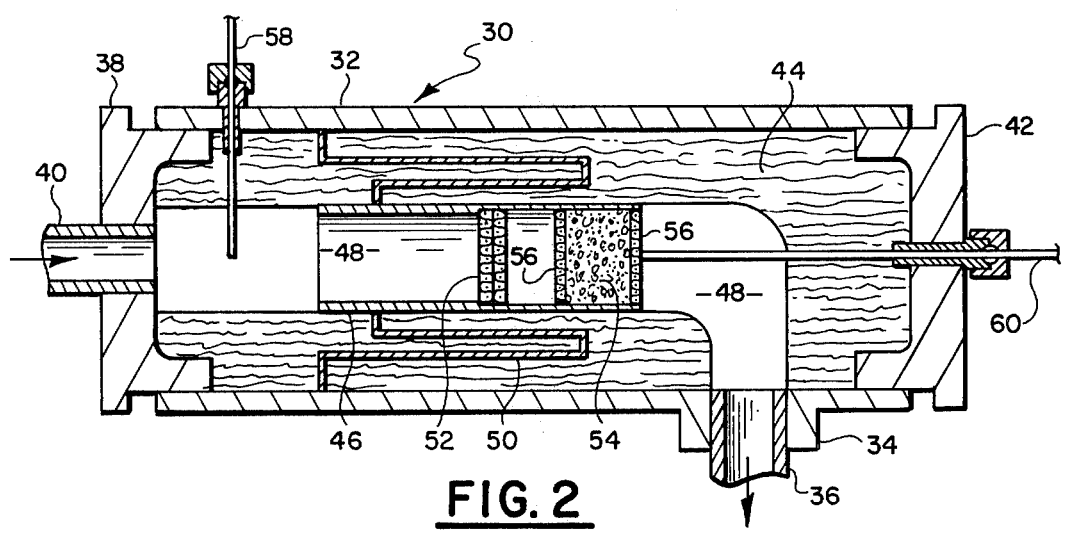
FIG. 2 is a cross-section of an instrument constructed in accordance with the present invention.

Referring now to FIG. 2, therein is depicted a preferred embodiment of the apparatus of the present invention. In the apparatus depicted in FIG. 2 the heating means is separate and not shown in the interest of clarity. The apparatus designated 30 comprises an elongated generally cylindrical metal housing 32, which has an opening 34 for receiving in sealing engagement an outlet conduit member 36. The apparatus further includes an end member 38, which is in sealing engagement with housing 32 and has an opening therein for receiving an inlet conduit member 40. The other end of housing 32 is closed with end member 42. Contained within housing 32 is a body of thermal insulating material 44 and an intermediate conduit member 46, which together form a gas passageway 48, which interconnects and provides the sole source of fluid communication between inlet conduit member 40 and outlet conduit member 36.

Intermediate conduit member 46 is retained in position by support and flow restricting member 50. Support member 50 defines a long tortuous path intermediate housing 32 and member 46, the purpose of which is to prevent gas flow around member 46 and to eliminate or substantially minimize any heat transfer between the gas in passageway 48 and metal housing 32, including the ambient surroundings.

Located within intermediate member 46 in the gas passageway are one or more perforate metal heat shields 52 downstream of which are a pair of spaced apart perforate supports 56 for retaining therebetween a body of particulate catalyst material 54. The apparatus 30 also is provided with an inlet temperature sensor and connector assembly 58, which extends into an upstream portion of the gas passageway 48 and a downstream temperature sensor and connector assembly 60, which extends through end member 42 with the sensor portion being positioned adjacent the body of particulate catalyst material for sensing the temperature of the gas passing therethrough.

While the manner in which the various members are secured in sealing engagement with one another and fixed to one another is not specified, numerous methods will be readily apparent to those versed in the art. For example, the various members could be welded or connected by mating threaded fasteners, welding, or bonded with high temperature epoxies and the like. Further, it will be apparent that the body of thermal insulating material could be formed in solid molded sections, and the end member 42 and a section of the thermal insulating material made removable to provide access to the body of particulate catalyst material to facilitate replacement of the catalyst, should such be desired.

EXAMPLE

Two devices were constructed in accordance with the present invention (substantially the same as that depicted in FIG. 2) from threaded pipe fittings. The gas heater 26 consists of a suitably insulated electric resistance type heater wrapped around a section of pipe through which the inlet gas passes. The power to the heater was manually adjusted in this example. However, numerous commercially available automatically controlled heaters are known to those versed in the art. The thermocouples used to measure inlet and outlet temperatures (58 and 60) are Type K, Chromel-Alumal, having a 1/16-inch diameter metal sheath. Five stainless steel 16-mesh (U.S. Sieve size) screens were used as the thermal shields. The same screen material was used to contain the catalyst in a bed which was about 1 inch in diameter by 1 inch long. The particulate catalyst was in the form of right circular cylinders $\frac{1}{8}$ of an inch in diameter by $\frac{1}{8}$ of an inch long. The outer surfaces comprised a mixture of platinum and palladium as the catalyst material.

A separate calibration test was made on each device. The relative humidity of the gas (hydrogen in air) used was about 30%. The gas was heated to a temperature of about 250° F. prior to entry into the apparatus to provide a gas stream having the desired low relative humidity. Prior to each calibration test, the heated gas stream was passed through the device without any hydrogen present to determine the device constant for the particular gas flowrate used. More particularly, with zero hydrogen concentration, there will be some heat loss from the apparatus such that the downstream temperature would be lower than the upstream temperature. This temperature differential decreases as the gas flowrate increases, but becomes a constant for any given installation. A gas stream containing varying concentrations of hydrogen in an excess of oxygen was passed through the device and the temperature differential measured. The true hydrogen concentration was determined using a gas chromatograph in the first test and hydrogen and air flowmeters in the second.

Figure 3:
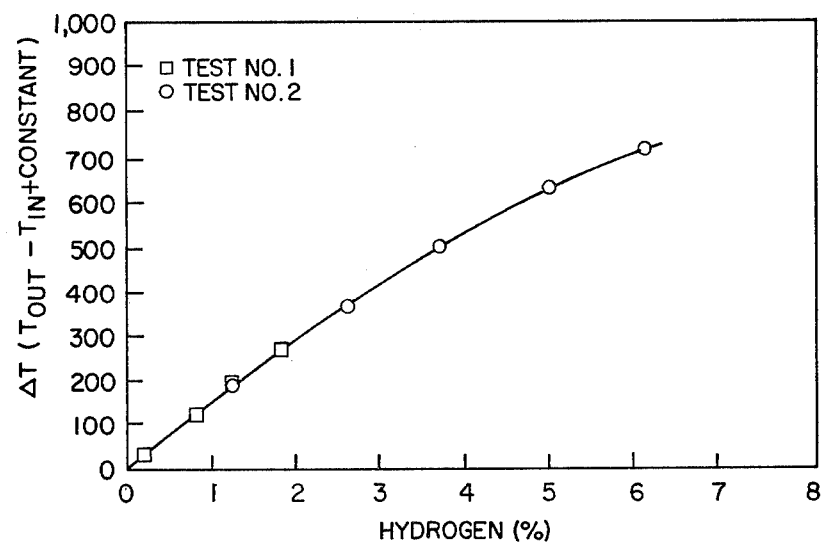
FIG. 3 is a typical calibration curve obtained with the present invention.

The flowrate in the second test was approximately twice that of the first test. The results of these tests are plotted in FIG. 3. From that figure it will be seen that the devices were sufficiently sensitive to indicate a change in hydrogen concentration lower than 0.1%. Careful measurements will indicate changes as low as 0.01% hydrogen. In addition, a high degree of repeatability is attained with devices constructed in accordance with the present invention. This is demonstrated by the fact that the two curves coincide with one another. This is particularly significant in view of the fact that two differenct devices and flowrates are involved, and the tests referred to occurred at substantially different points in time. Another significant advantage of the present invention is that the measurements are unaffected by minor variations in flow. More particularly, in accordance with the present methods and apparatus, a variation in flowrate of as much as 20% above or below the calibration flowrate results in an error of less than 0.02% hydrogen. Thus, the present method and apparatus may be practiced with an inexpensive flowmeter or a positive displacement blower without need of a flowmeter.

While certain exemplary embodiments of the present invention have been described with regard to the detection of hydrogen and oxygen, as well as the preferred catalyst materials therefor, it will be appreciated that the invention will also be applicable to the monitoring or detection of other constituents of a gas stream through the selection of an appropriate catalyst. Further, numerous variations of the details of construction of the apparatus described and depicted in the drawings will be apparent to those versed in the art. Thus, while the drawings and examples illustrating this invention have been described with respect to specific structures, gases, concentrations, temperatures and the like, the invention may be otherwise practiced as will be readily apparent to those skilled in this art. Accordingly, the invention is not to be limited by the illustrative specific embodiments disclosed herein; rather, its scope should be determined in accordance with the following claims.

What is claimed is:

1. An apparatus for monitoring a gas stream comprising:
   (a) a conduit member defining a single gas passageway extending therethrough and having opposite ends, a gas inlet means adjacent one of the ends, and a gas outlet means adjacent the other of the ends, said gas passageway defining the sole means of fluid communication between said gas inlet and gas outlet means;
   (b) at least two temperature sensors, one located adjacent the gas inlet means and the other located adjacent the gas outlet means of said conduit member for sensing the temperature of a gas passing therethrough;
   (c) a body of a particulate catalyst located in the gas passageway of said conduit member intermediate the two temperature sensors;
   (d) at least one perforate heat shield located in the gas passageway of said conduit member between the body of particulate catalyst and the gas inlet temperature sensor for reducing the transfer of radiant thermal energy from the body of particulate catalyst material to the gas inlet temperature sensor; and
   (e) heater means for heating the gas stream to be monitored to a desired temperature prior to its entry into contact with the gas inlet temperature sensor.

2. The apparatus of claim 1 wherein the catalyst material is selected from the group consisting of platinum, palladium, and combinations thereof.

3. The apparatus of claim 1 wherein said conduit member is surrounded by a metal housing.

4. The apparatus of claim 1 wherein said conduit member is formed from a thermal insulating material.

5. The apparatus of claim 3 wherein said conduit member is thermally insulated from said metal housing.

6. The apparatus of claim 1 wherein at least one of said gas inlet and gas outlet means are in axial alignment with the gas passageway of the conduit member.

7. An apparatus for monitoring the hydrogen or oxygen content of a gas stream in which one of said hydrogen or oxygen is present in an excess over the other, which apparatus comprises:
   (a) an elongated conduit member defining a single gas passageway extending axially therethrough and having opposite ends, a gas inlet adjacent one of the ends and a gas outlet adjacent the other of the ends, said single gas passageway defining the sole means of fluid communication between said gas inlet and outlet;
   (b) a gas inlet temperature sensor located in the gas passageway adjacent the inlet end of the conduit member for sensing the temperature of a gas passing therethrough;
   (c) a gas outlet temperature sensor located in the gas passageway adjacent the gas outlet end of the conduit member for sensing the temperature of a gas passing therethrough;
   (d) a body of particulate catalyst material located in the gas passageway intermediate the gas inlet and gas outlet temperature sensors, said body of particulate catalyst material being located in the proximity of the gas outlet end of the conduit member, and having an exposed surface selected from the group of materials consisting of palladium, platinum and combinations thereof;
   (e) a perforate metal heat shield, located in the passageway of the conduit member between the body of particulate catalyst material and the gas inlet temperature sensor, for shielding the gas inlet temperature sensor from radiant thermal energy from the body of particulate catalyst material; and
   (f) means associated with the conduit member for heating the gas stream to a desired temperature prior to its entry into the gas inlet, said temperature being substantially above ambient temperature.

8. The apparatus of claim 7 wherein said conduit member is surrounded by a metal housing.

9. The apparatus of claim 8 wherein said conduit member is formed from a thermal insulating material.

10. The apparatus of claim 8 wherein said housing is in a spaced relation from said conduit member and a thermal barrier means is located in the space between them.

11. A method for monitoring a component of a gas stream comprising the sequential steps of:
   (a) heating the gas stream to a desired temperature,
   (b) introducing the gas stream into a single, axially extending, thermally insulated gas passageway,
   (c) sensing the temperature of the heated gas stream,
   (d) passing the gas stream through at least one perforate heat shield,
   (e) passing the gas through a bed of particulate catalyst, which is spaced from said perforate metal shield,
   (f) sensing the temperature of the gas exiting the catalyst bed,
   (g) determining the concentration of the component of the gas stream as a function of the difference between the temperatures in steps (c) and (f), and
   (h) discharging the gas stream from the thermally insulated gas passageway.

12. A method of monitoring the hydrogen content of a gas stream containing the same in an excess of oxygen comprising the sequential steps of:
   (a) heating the gas stream to a temperature substantially above ambient temperature,
   (b) introducing the heated gas stream into a single, axially extending thermally insulated gas passageway,
   (c) sensing the temperature of the heated gas stream,
   (d) passing the gas stream through a perforate metal heat shield,
   (e) passing the gas stream through a bed of a particulate catalyst, said catalyst being selected from a group consisting of platinum, palladium, and combinations thereof,
   (f) sensing the temperature of the gas exiting the catalyst bed,
   (g) determining the hydrogen content as a function of the difference between the temperatures in steps (c) and (f), and
   (h) discharging the gas stream from the thermally insulated gas passageway.

* * * * *